United States Patent [19]

Loebenberg et al.

[11] 4,299,845
[45] Nov. 10, 1981

[54] DERMATOLOGICAL COMPOSITIONS AND METHODS OF USE THEREFOR

[75] Inventors: David Loebenberg, Monsey, N.Y.; Elijah H. Gold, West Orange, N.J.

[73] Assignee: Schering Corporation, Kenilworth, N.J.

[21] Appl. No.: 139,918

[22] Filed: Apr. 14, 1980

[51] Int. Cl.³ .................. A61K 31/165; A61K 31/275
[52] U.S. Cl. .................................... 424/324; 424/304
[58] Field of Search ............................. 424/304, 324; 260/562 R

[56] References Cited

U.S. PATENT DOCUMENTS

| | | | |
|---|---|---|---|
| 2,776,241 | 1/1957 | Priewe et al. | 260/562 K |
| 2,995,605 | 8/1961 | Siegrist et al. | 260/562 K |
| 3,857,879 | 12/1974 | Abramitis | 260/561 |
| 3,946,074 | 3/1976 | Abramitis | 260/561 K |
| 3,965,175 | 6/1976 | Gold | 424/324 |
| 4,143,070 | 3/1979 | Walker | 260/562 R |

*Primary Examiner*—Douglas W. Robinson
*Attorney, Agent, or Firm*—Mary S. King; Barbara L. Renda

[57] ABSTRACT

The present invention relates to topical compositions and methods of use utilizing compounds of the formula

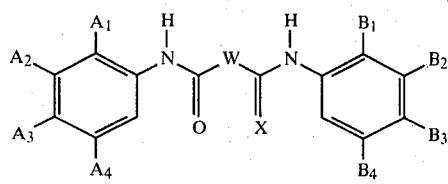

wherein
X is oxygen or sulfur;
W is a bridge group of the formulae

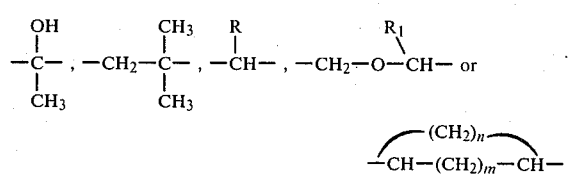

wherein R is hydrogen alkyl of 1 to 7 carbon atoms, cycloalkyl of 4–8 carbon atoms, cycloalkenyl of 5–8 carbon atoms, polyfluoroalkyl of 1–4 carbon atoms, phenyl, benzyl or alkoxycarbonylmethyl; $R_1$ is hydrogen or alkyl of 1–7 carbon atoms; m is 0–2; n is 1–4; with the proviso that m+n is 3–5; and $A_1$, $A_2$, $A_3$, $A_4$, $B_1$, $B_2$, $B_3$, and $B_4$ are independently selected from the group consisting of hydrogen, methyl, cyano, nitro, polyfluoroalkyl of 1–3 carbon atoms, chloro, bromo, fluoro and alkylthio, with the proviso that 2–5 of there are hydrogen of which at least one of $A_1$, $A_2$, $A_3$ and $A_4$ and at least one of $B_1$, $B_2$, $B_3$ and $B_4$ is hydrogen.

26 Claims, No Drawings

DERMATOLOGICAL COMPOSITIONS AND METHODS OF USE THEREFOR

The present invention relates to the use of malonamides and topical compositions thereof for the treatment of dermatological disorders.

More particularly, the present invention relates to topical compositions and methods of use utilizing compounds of the formula

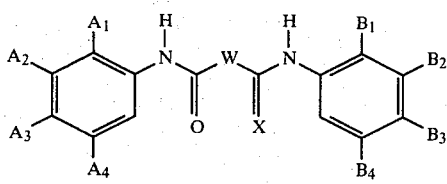

wherein
X is oxygen or sulfur;
W is a bridge group of the formulae

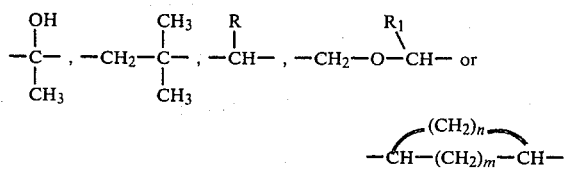

wherein R is hydrogen alkyl of 1 to 7 carbon atoms, cycloalkyl of 4-8 carbon atoms, cycloalkenyl of 5-8 carbon atoms, polyfluoroalkyl of 1-4 carbon atoms, phenyl, benzyl or alkoxycarbonylmethyl; $R_1$ is hydrogen or alkyl of 1-7 carbon atoms; m is 0-2; n is 1-4; with the proviso that m+n is 3-5; and $A_1$, $A_2$, $A_3$, $A_4$, $B_1$, $B_2$, $B_3$, and $B_4$ are independently selected from the group consisting of hydrogen, methyl, cyano, nitro, polyfluoroalkyl of 1-3 carbon atoms, chloro, bromo, fluoro and alkylthio, with the proviso that 2-5 of these are hydrogen of which at least one of $A_1$, $A_2$, $A_3$ and $A_4$ and at least one of $B_1$, $B_2$, $B_3$ and $B_4$ is hydrogen.

Preferred compounds of this invention are those of formula I wherein W is a group of the formula

wherein R is alkyl of 1-4 carbon atoms, cyclopentenyl or benzyl. Particularly preferred are those compounds wherein W is

wherein R is alkyl of 1-4 carbons atoms, cyclopentenyl or benzyl, and $A_1$, $A_2$, $A_3$, $A_4$, $B_1$, $B_2$, $B_3$ and $B_4$ are selected from the group consisting of hydrogen, nitro, trifluoromethyl and chloro. Certain substituent patterns on the two ring systems are preferred; and compounds wherein $A_2$ and $B_2$ are other than hydrogen are highly preferred, for instance, the compounds wherein $A_1$ and $B_1$ are hydrogen and $A_2$, $A_3$, $A_4$, $B_2$, $B_3$ and $B_4$ are all chloro; the compounds wherein $A_1$, $A_3$, $B_1$ and $B_3$ are all hydrogen and $A_2$, $A_4$, $B_2$ and $B_4$ are all trifluoromethyl; as well as compounds wherein $A_1$, $A_4$ and $B_1$ are hydrogen and $A_2$, $A_3$, $B_2$, $B_3$ and $B_4$ are independently trifluoromethyl, chloro, nitro, bromo, fluoro or methylthio.

Especially preferred compounds for use in topical compositions for the treatment of acne are N,N'-bis-(3,4,5-trichlorophenyl)methylmalonamide, N,N'-bis-[3,4-bis-(trifluoromethyl)phenyl]methylmonothiomalonamide, N,N'-bis-[3,5-bis-(trifluoromethyl)phenyl]methylmalonamide and N,N'-bis-[3,5-bis-(trifluoromethyl)phenyl]methylmalonamide.

Especially preferred compounds for use in topical compositions for the treatment of gram-positive bacterial infections are N,N'-bis-[3,5-bis-(trifluoromethyl)phenyl]methylmalonamide, N,N'-bis-[3,4-bis-(trifluoromethyl)phenyl]methylmonothiomalonamide, N-[3,4-bis-(trifluoromethyl)phenyl]-N'-(5-chloro-2-nitrophenyl)methylmalonamide, N,N'-bis-(3-trifluoromethyl-4-nitrophenyl)benzylmalonamide, and N-(3-trifluoromethyl-4-nitro-phenyl)-N'-[3,5-bis-(trifluoromethyl)phenyl]methylmalonamide.

Especially preferred compounds for use in topical compositions for the treatment of fungal infections are N-[3,4-bis-(trifluoromethyl)phenyl]-N'-(5-chloro-2-nitrophenyl)methylmalonamide, N,N'-bis-[3,4-bis-(trifluoromethyl)phenyl]methylmonothiomalonamide and N-(3-trifluoromethyl-4-nitrophenyl)-N'-(3-fluoro-4-nitrophenyl)methylmalonamide.

The term "alkyl" as used herein denotes alkyl groups containing 1-6 carbon atoms and includes methyl, ethyl, propyl, butyl, pentyl and hexyl, and the corresponding branched chain isomers thereof. Likewise, "alkoxy" encompasses methoxy, ethoxy, propoxy and butoxy and the corresponding branched chain isomers thereof.

Representative compounds useful in this invention include:
N,N'-bis-(3,4,5-trichlorophenyl)methylmalonamide;
N,N'-bis-[3,4-bis(trifluoromethyl)phenyl]-methylmonothiomalonamide;
N,N'-bis-[3,4-bis(trifluoromethyl)phenyl]methylmalonamide;
N,N'-bis-(3-trifluoromethyl-4-nitrophenyl)-(2-cyclopenten-1-yl)malonamide;
N,N'-bis-[3',5'-bis(trifluoromethyl)]methylmalonamide;
N,N'-bis-[3,4-bis-(trifluoromethyl)phenyl]-(2-cyclopenten-1-yl)malonamide;
N,N'-bis-[3,4-bis-(trifluoromethyl)phenyl]ethylmalonamide;
N,N'-bis-[3,4-bis-(trifluoromethyl)phenyl]benzylmalonamide;
N-[3,4-bis-(trifluoromethyl)phenyl]-N'-[3,5-bis-(trifluoromethyl)phenyl]methylmalonamide;
N-[3,4-bis-(trifluoromethyl)phenyl]-N'-(3-trifluoromethyl-4-nitrophenyl)methylmalonamide;
N-[3,4-bis-(trifluoromethyl)phenyl]-N'-(3,4-dichlorophenyl)methylmalonamide;
N-(3-trifluoromethyl-4-nitrophenyl-N'-(3,4,5-trichlorophenyl)methylmalonamide;
N-(4-nitro-3-trifluoromethylphenyl)-N'-(4-chloro-3-trifluoromethylphenyl)methylmalonamide;
N-(4-nitro-3-trifluoromethylphenyl)-N'-(3,4-dichlorophenyl)methylmalonamide;
N-[3,4-bis-(trifluoromethyl)phenyl]-N'-(4'-methylthio-3'-trifluoromethyl)phenylmethylmalonamide;
N,N'-bis-(3-trifluoromethyl-4-nitrophenyl)ethylmalonamide;

N,N'-bis-(3-trifluoromethyl-4-nitrophenyl)-n-butylmalonamide;
N,N'-bis-(3-trifluoromethyl-4-nitrophenyl)benzylmalonamide;
N-(3-trifluoromethyl-4-nitrophenyl)-N'-[3,5,-bis-(trifluoromethyl)phenyl]methylmalonamide;
N,N'-bis-(3-trifluoromethyl-4-nitrophenyl)propylmalonamide;
N,N'-bis-(3-trifluoromethyl-4'-nitrophenyl)isobutylmalondiamide;
N,N'-bis-(3'-trifluoromethyl-4'-nitro)methylmalondiamide;
N,N'-bis-(3-nitro-4-chlorophenyl)methylmalonamide;
N,N'-bis-(3,4-dichlorophenyl)methylmalonamide;
N,N'-bis-[3,4-bis-(trifluoromethyl)phenyl]phenylmalonamide;
N,N'-bis-[3,5-(trifluoromethyl)phenyl]ethylmalonamide;
N,N'-bis-[3,5-bis-(trifluoromethyl)phenyl]benzylmalonamide;
N,N'-bis-(3-trifluoromethyl-4-nitrophenyl)diglycolamide;
N,N'-bis-(3-trifluoromethyl-4-nitrophenyl)-trans-1,2-cyclohexane dicarboxamide;
N,N'-bis-[3,4-bis-(trifluoromethyl)phenyl]-2,2-dimethylsuccinamide;
N-[3,4-bis-(trifluoromethyl)phenyl]-N'-(3-nitrophenyl)methylmalonamide;
N-[3,4-bis-(trifluoromethyl)phenyl]-N'-(3-trifluoromethylphenyl)methylmalonamide;
N-[3,4-bis-(trifluoromethyl)phenyl]-N'-(4-chloro-3-nitrophenyl)methylmalonamide;
N-[3,4-bis-(trifluoromethyl)phenyl]-N'-(5-chloro-2-nitrophenyl)methylmalonamide;
N-[3,4-bis-(trifluoromethyl)phenyl]-N'-(4-chlorophenyl)methylmalonamide;
N-[3,4-bis-(trifluoromethyl)phenyl]-N'-(4-dichlorophenyl)methylmalonamide;
N-[3,4-bis-(trifluoromethyl)phenyl]-N'-(2,4-dichlorophenyl)methylmalonamide;
N-[3,4-bis-(trifluoromethyl)phenyl]-N'-(3-chloro-4-methylphenyl)methylmalonamide;
N-[3,4-bis-(trifluoromethyl)phenyl]-N'-(4-nitrophenyl)methylmalonamide;
N-[3,4-bis-(trifluoromethyl)phenyl]-N'-(4-bromophenyl)methylmalonamide;
N-[3,4-bis-(trifluoromethyl)phenyl]-N'-(4-chloro-3-trifluoromethylphenyl)methylmalonamide;
N-[3,4-bis-(trifluoromethyl)phenyl]-N'-phenylmethylmalonamide;
N-[3,4-bis-(trifluoromethyl)phenyl]-N'-(p-carboethoxyphenyl)methylmalonamide;
N-[3,4-bis-(trifluoromethyl)phenyl]-N'-(m-carboethoxyphenyl)methylmalonamide;
N-[3,4-bis-(trifluoromethyl)phenyl]-N'-(2-trifluoromethyl-4-nitrophenyl)methylmalonamide;
N-[3,4-bis-(trifluoromethyl)phenyl]-N'-(2-nitro-4-trifluoromethylphenyl)methylmalonamide;
N-[3,4-bis-(trifluoromethyl)phenyl]-N'-(2,4-dinitrophenyl)methylmalonamide;
N-(4-nitro-3-trifluoromethyl)-N'-(3,4-dichlorophenyl)methylmalonamide;
N-[3,4-bis-(trifluoromethyl)phenyl]-N'-(4-methylsulfonyl-3-trifluoromethylphenyl)methylmalonamide;
N-(3-trifluoromethyl-4-nitrophenyl)-N'-(3-trifluoromethyl-4'-methylthiophenyl)methylmalonamide;
N,N'-bis-[3,4-bis-(trifluoromethyl)phenyl]methyltartronamide;
N-(3-trifluoromethyl-4-nitrophenyl)-N'-(4-nitrophenyl)methylmalonamide;
N-(3-trifluoromethyl-4-nitrophenyl)-N'-(3-nitro-4-chlorophenyl)methylmalonamide;
N-(3-trifluoromethyl-4-nitrophenyl)-N'-(3-chloro-4-nitrophenyl)methylmalonamide;
N-(3-trifluoromethyl-4-nitrophenyl)-N'-(3-chlorophenyl)methylmalonamide;
N-(3-trifluoromethyl-4-nitrophenyl)-N'-(3-fluoro-4-nitrophenyl)methylmalonamide;
N-(3-trifluoromethyl-4-nitrophenyl)-N'-(2-chloro-5-nitrophenyl)methylmalonamide;
N-(3-trifluoromethyl-4-nitrophenyl)-N'-(4-cyanophenyl)methylmalonamide;
N-(3-trifluoromethyl-4-nitrophenyl)-N'-(2-chloro-4-nitrophenyl)methylmalonamide;
N-(3-trifluoromethyl-4-nitrophenyl)-N'-(3-trifluoromethylphenyl)methylmalonamide;
N-(3-trifluoromethyl-4-nitrophenyl)-N'-(2-trifluoromethyl-4-nitrophenyl)methylmalonamide;
N-(3-chloro-4-nitrophenyl)-N'-(3-chlorophenyl)methylmalonamide;
N-(3-chloro-4-nitrophenyl)-N'-(4-chloro-3-nitrophenyl)methylmalonamide;
N-(3-chloro-4-nitrophenyl)-N'-(4-nitrophenyl)methylmalonamide;
N-3-nitrophenyl-N'-(3-chloro-4-nitrophenyl)methylmalonamide;
N-(2,4,5-trichlorophenyl)-N'-[3,5-bis-(trifluoromethyl)phenyl]methylmalonamide;
N-(2,4,5-trichlorophenyl)-N'-(3-chloro-4-nitrophenyl)methylmalonamide;
N-(2,4,5-trichlorophenyl)-N'-(3-trifluoromethyl-4-nitrophenyl)methylmalonamide;
N-(4-nitrophenyl)-N'-(2,4,5-trichlorophenyl)methylmalonamide.
N-(4-nitrophenyl)-N'-(3-chlorophenyl)methylmalonamide;
N,N'-(3-methylphenyl)methylmalonamide;
N-(3-chloro-4-nitrophenyl)-N'-(4-chlorophenyl)methylmalonamide;
N-[3,4-bis-(trifluoromethyl)phenyl]-N'-(2,5-dimethyl-4-nitrophenyl)methylmalonamide;
N-[3,4-bis-(trifluoromethyl)phenyl]-N'-(3-methylthiophenyl)methylmalonamide; and
N,N-bis-[3,4-bis-(trifluoromethyl)phenyl]-n-butylmalonamide.

Many of the malonamides of formula I are described in U.S. Pat. No. 3,965,175 as agents useful in the treatment of poultry coccidiosis.

Most surprisingly, the instant malonamides of formula I have been found to be useful agents for topical treatment of dermatological disorders, particularly those such as acne, gram-positive bacterial, and fungal infections. More specifically, the malonamides of formula I have been found to be inhibitors of the bacterium *Propionibacterium acnes* and also to inhibit sebaceous gland lipase. These qualities make them effective in the treatment of acne when formulated for topical application. Additionally, the compounds are topically active against such gram-positive bacteria as Staphylococcus, Streptococcus, and Bacillus, yeasts such as Candida and Saccharomyces, and dermatophytes such as Epidermophyton, Trichophyton and Microsporum.

The potency of the malonamides of formula I against *P. acnes*, gram-positive bacteria and fungi was determined using in vitro dilution tests for minimum inhibitory concentrations (MICs) in a conventional manner using Mueller-Hinton Broth at the appropriate pH, in volumes of 3-5 mls per tube. Innocula were obtained by diluting cultures grown either overnight (gram-positives, P. acnes and yeasts) or for a number of days (dermatophytes). Tubes were incubated either aerobically or anaerobically at 37° C. or room temperature. Endpoints were determined after 24, 48 or 72 hours. Using this assay, the malonamides were found to possess MICs against P. acnes, gram-positive bacteria and fungi at levels of <0.01 to 10 mcg/ml.

The inhibitory activity of sebaceous gland lipase by the malonamides of formula I was determined by the following procedure:

The lipase was prepared by excising both flank organs from 100 gram male golden syrian hamsters (Lakeview) and homogenizing each organ in 3 ml water using a glass on glass homogenizer.

The enzyme homogenate (0.5 ml) was allowed to react for 15 min at room temperature with 0.8 ml tris acetate buffer (pH 8.4) and 0.2 ml of 4-methylumbelliferone palmitate (4 MUP-50 umole/L). The fluorescense of the released umbelliferone (ex=360 nm, em=450 nm) was recorded using a Farrand Fluorometer.

In order to test for inhibition of the enzyme the test compounds were solubilized in propylene glycol:ethanol (1:1) and a 50 ul aliquot was added to the enzyme reaction mixture.

The IC$_{50}$ (concentration yielding 50% inhibition of the enzyme) was calculated using least squares regression from results obtained by measuring inhibition at a number of concentrations. Many of the malonamides of formula I were found to cause about 50% inhibition of the sebaceous gland lipase when tested in this assay at a concentration of $1 \times 10^{-4}$ M.

The topical compositions of this invention comprise the malonamides of formula I in a vehicle suitable for topical administration so as to afford topical pharmaceutical compositions useful in the treatment of dermatological disorders. Topical compositions are exemplified by ointments, creams, lotions, aerosols, gels, or soaps. Such compositions will normally be based upon standard dermatological carriers which are pharmaceutically acceptable and cosmetically elegant, such as those selected from pharmaceutically acceptable vegetable oils, pharmaceutically acceptable polyalkylene glycols, isopropanol, gelatin, benzyl alcohol, gums, glycerol and petrolatum. Optionally, the compositions may contain preservatives, aerosol propellants, such as hydrocarbons, and coloring, thickening, suspending, dispersing, emulsifying, wetting, stabilizing, and buffering agents. These formulations are envisioned to contain the malonamide of formula I in an amount of from about 0.1 to about 3 percent by weight for topical application. The compositions of this invention are thus especially useful in the treatment of dermatological disorders such as acne, gram-positive bacterial infections and fungal infections.

The compounds of formula I wherein X is oxygen and W is other than

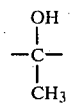

may be conveniently prepared by reaction of the aniline of the formula

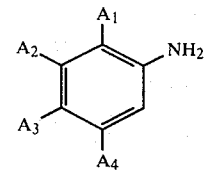

(II)

wherein A$_1$, A$_2$, A$_3$, and A$_4$ are as hereinbefore defined with an acid halide-ester of the formula

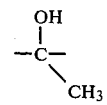

(III)

wherein W is other than

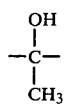

and Z is chlorine or bromine, and V is lower alkoxy, aryloxy or aralkyloxy, to afford an intermediate of the formula

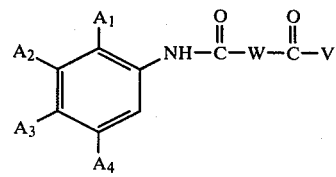

(IV)

wherein W is other than

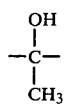

and A$_1$, A$_2$, A$_3$, A$_4$ and V are as hereinbefore defined. Preferably, the acid halide-ester of Formula III is added in excess, and upon completion of the reaction, is removed by distillation. The intermediate of Formula IV may be isolated and purified, but preferably, is hydrolyzed further, without isolation, to the corresponding malonamic acid (IV,V=H) which in turn is converted to the corresponding acid halide (IV,V=chlorine or bromine) and reacted with an aniline of the formula

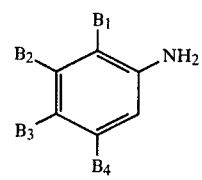

wherein $B_1$, $B_2$, $B_3$ and $B_4$ are as hereinabove defined to afford the desired compound of Formula I wherein X is oxygen and W is other than

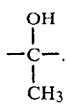

Suitable solvents for use in this reaction sequence are organic solvents such as benzene, toluene, ethyl ether or tetrahydrofuran. Depending on the nature of the reactants, the reaction is conducted at temperatures ranging from room temperature to the reflux temperature of the solvent.

The intermediates of formula IV also exhibit good anti-acne activity and are thus also utilizable in topical compositions.

Alternatively, the compound of Formula I wherein Y is oxygen, W is

and $A_1$, $A_2$, $A_3$ and $A_4$ are identical to $B_1$, $B_2$, $B_3$ an $B_4$ may be conveniently prepared by condensation of an aniline of the formula

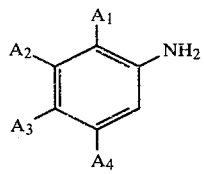

wherein
$A_1$ is identical to $B_1$;
$A_2$ is identical to $B_2$;
$A_3$ is identical to $B_3$;
$A_4$ is identical to $B_4$;
and $A_1$, $A_2$, $A_3$, $A_4$, $B_1$, $B_2$, $B_3$ and $B_4$ are all as hereinbefore; with a malonic halide of the formula

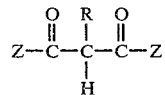

wherein Z is as hereinbefore defined. This condensation is conducted in a suitable solvent, preferably at elevated temperatures, i.e., up to the boiling point of the solvent.

Other methods for the preparation of the compound wherein X is oxygen and W is

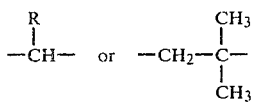

are disclosed in U.S. Pat. No. 3,965,175(1976).

The compounds of Formula I wherein X is oxygen and W is

may be prepared by treatment of the corresponding compounds wherein X is oxygen, W is

and R is methyl with sodium hydride, or a similar strong base, followed by treatment with a suitable oxidizing agent such as dibenzoyl peroxide, to afford the benzoate ester of the desired compound. The benzoate ester is then removed using a strong aqueous base such as sodium or potassium hydroxide to afford the desired compound of Formula I wherein X is oxygen and W is

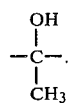

The compounds of formula I wherein X is sulfur may be prepared by treatment of the corresponding compound wherein X is oxygen with phosphorus pentasulfide. This reaction is typically conducted in an anhydrous solvent such as pyridine or the like at temperatures from about 40° C. to reflux of the particular solvent.

Alternately, the compounds of formula I wherein X is sulfur may be prepared by the process described above by reaction of the compound of the formula IV wherein the anilide carbonyl is a thio-carbonyl group. The starting 3-thiomalonamic acids required for the process are described in *J. Org. Chem.* 45, 1109–1113 (1980).

The following examples describe in detail the preparation of representative compounds and compositions illustrative of the present invention. It will be apparent to those skilled in the art that many modifications, both of materials and methods, may be practiced without departing from the purpose and intent of this disclosure.

EXAMPLE 1

Preparation of
N,N'-BIS-3,4-BIS-(TRIFLUOROMETHYL)-PHENYL]-2,2 DIMETHYLSUCCINAMIDE Reflux a mixture of 2.01 g of dimethyl succinic acid and 20 g of thionyl chloride in 75 ml of dry ether for four hours. Remove the excess ether and thionyl chloride in vacuo and dissolve the residue in 75 ml of fresh dry ether. Add 3 g of 3,4-bis-trifluoromethylaniline and stir at room temperature for 48 hours. Remove the ether in vacuo and triturate the residue with hexane. Filter and digest the solid residue in 30 ml of boiling chloroform for 3 hours. Filter and obtain the analytically pure title compound of this example, m.p. 184.5°–185.5° C.

EXAMPLE 2

Preparation of
N,N'-BIS-[3,4-BIS-(TRIFLUOROMETHYL)-
PHENYL]METHYLMONOTHIOMALONAMIDE Reflux, with stirring, 5.0 g of N,N'-bis-[3,4-bis-(trifluoromethyl)phenyl]methylmalonamide and 0.9 g of $P_2S_5$ in 50.0 ml of dry pyridine for 7.5 hours. Partition the reaction mixture between ether and 4 N HCl. Wash the ether layer with 4 N HCl until the pyridine is removed, then wash with water and dry over sodium sulfate. Filter, remove the ether in vacuo and chromatograph the residue on acidic alumina. Elute with hexane/dichloromethane (1:1), followed by dichloromethane. Obtain the analytically pure title compound [Rf ca. 0.4 (tlc-silica gel chloroform)] by recrystallization from chloroform, m.p. 156°–158° C.

EXAMPLE 3

Preparation of
N,N'-BIS-[3,4-BIS-(TRIFLUOROMETHYL)-
PHENYL]METHYLTARTRONAMIDE a. N,N'-bis-[3,4-bis(trifluoromethyl)phenyl]methyltartronamide benzoate ester.

To a stirred suspension of 0.515 g of sodium hydride (57% in mineral oil) in 10 ml of dry dimethylformamide, under a nitrogen atmosphere, add dropwise a solution of 6.0 g N,N'-bis-[3,4-bis-(trifluoromethyl)phenyl]methylmalonamide dissolved in 35 ml of dry dimethylformamide. Upon cessation of gas evolution, cool the resulting orange solution to about 0°–5° C. and add dropwise a solution of 2.8 g dibenzoyl peroxide in 30 ml of dry dimethylformamide. Stir the resulting white suspension for 16 hours at room temperature under a nitrogen atmosphere, quench with aqueous sodium bisulfite and extract with ether. Wash the ether extract with water, dry over sodium sulfate and remove the ether in vacuo. Chromatograph the residue on 200 g of acidic alumina and elute with hexane/methylene chloride (3:2) to separate the product from unreacted starting material. Recrystallize this material from 1:2 benzene/hexane to give the title compound [$R_f$=0.55 (tlc-silica gel, 7:1 chloroform/hexane].

b. N,N'-bis-[3,4-bis-(trifluoromethyl)phenyl]methyltartronamide.

To a stirred solution of 5.2 g of the product of paragraph a in 40 ml of methanol, add 0.32 of sodium hydroxide in 10 ml of water and stir for 16 hours. Partition between water and ether. Wash the ether extract with brine, dry over sodium sulfate, filter and remove the ether in vacuo. Recrystallize the residue from 30 ml of benzene/hexane (1:1) and obtain the analytically pure title compound, m.p. 118°–119° C.

EXAMPLE 4

Preparation of
N,N'-BIS-(3-TRIFLUOROMETHYL-4-NITRO-
PHENYL)DIGLYCOLAMIDE

Reflux a mixture of 11.97 g (0.07 mole) of diglycolic acid dichloride and 28.84 g (0.14 mole) of 3-trifluoromethyl-4-nitroaniline in 250 ml of benzene for 1 hour. Isolate the solid product of this example by filtration and obtain analytically pure material by recrystallization from benzene-methanol followed by crystallizatin from pure methanol, mp 137°–138° C.

EXAMPLE 5

Preparation of
N,N'-BIS-(3-TRIFLUOROMETHYL-4-NITRO-
PHENYL)TRANS-1,2-CYCLOHEXANEDICAR-
BOXAMIDE Reflux a mixture of 16.73 g (0.08 moles) of trans-1,2-cyclohexane dicarboxylic acid chloride and 32.96 g (0.16 moles) of 3-trifluoromethyl-4-nitroaniline in 250 ml of benzene for 1.5 hours. Isolate the solid product of this example by filtering, washing well with hot benzene followed by ether and obtain analytically pure material by recrystallization from benzenemethanol, mp 249.5°–251° C. (dec.).

The following formulations are to exemplify some of the dosage forms in which the compounds of this invention may be employed. In each, the active ingredient is designated by the term "Drug" which is meant to indicate one of the following compounds: N,N'-bis-[3,5-bis-(trifluoromethyl)phenyl]methylmalonamide, N,N'-bis-[3,4-(trifluoromethyl)phenyl]methylmonothiomalonamide, or N,N'-bis-(3,4,5-trichlorophenyl)methylmalonamide. It will be appreciated, however, that each of these compounds may be replaced by equally effective quantities of other compounds defined by formula I.

EXAMPLE 6

| Cream Formulation | mg/g |
|---|---|
| Drug | 1.0 |
| Cetyl Esters Wax | 20.0 |
| Cetyl Stearyl Alcohol | 100.0 |
| Sorbitan Monostearate | 25.0 |
| Polysorbitan 60 | 20.0 |
| Cetyl Dodecanal | 100.0 |
| Propylene Glycol | 100.0 |
| Benzyl Alcohol | 10.0 |
| Purified Water | To make 1 g |

EXAMPLE 7

| Cream Formulation | mg/g |
|---|---|
| Drug | 10.0 |
| Stearic Acid | 60.0 |
| Propylene Glycol Monostearte | 100.0 |
| Isopropyl Myristate | 50.0 |
| Propylene Glycol | 100.0 |
| Polyoxyethylene 20 Sorbitan Monopalmitate | 60.0 |
| Methylparaben | 1.0 |
| Butylparaben | 4.0 |
| Purified Water | To make 1 g |

EXAMPLE 8

| Gel Formulation | mg/g |
|---|---|
| Drug | 5.0 |
| Propylene Glycol | 50.0 |
| Hydroxypropyl Cellulose | 20.0 |
| Alcohol | To make 1g |

EXAMPLE 9

| Gel Formulation | mg/g |
|---|---|
| Drug | 2.5 |

-continued

| Gel Formulation | mg/g |
|---|---|
| Propylene Glycol | 350.0 |
| Alcohol | 350.0 |
| Carbomer 940 | 20.0 |
| Monoamylamine | 2.0 |
| Purified Water | To make 1 g |

EXAMPLE 10

| Lotion Formulation | mg/g |
|---|---|
| Drug | 5.0 |
| Ethyl Alcohol | 400.0 |
| Polyethylene Glycol 400 | 300.0 |
| Hydroxypropyl Cellulose | 5.0 |
| Propylene Glycol | To make 1 g |

What is claimed is:

1. A topical composition for the treatment of dermatological disorders selected from the group consisting of acne, gram-positive bacterial infections and fungal infections comprising a therapeutically effective amount of a compound of the formula

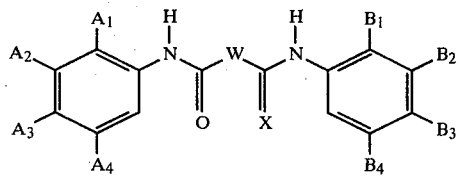

wherein
X is oxygen or sulfur;
W is a bridge group of the formula:

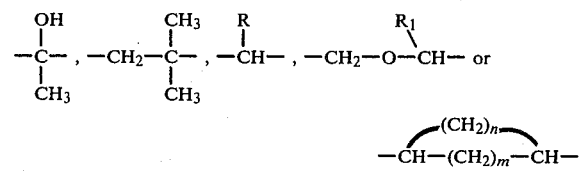

wherein R is hydrogen alkyl of 1 to 7 carbon atoms, cycloalkyl of 4-8 carbon atoms, cycloalkenyl of 5-8 carbon atoms, polyfluoroalkyl of 1-4 carbon atoms, phenyl, benzyl or alkoxycarbonylmethyl, $R_1$ is hydrogen or alkyl of 1 to 7 carbon atoms, m is 0-2, n is 1-4; with the proviso that m+n is 3-5; and $A_1$, $A_2$, $A_3$, $A_4$, $B_1$, $B_2$, $B_3$, and $B_4$ are independently selected from the group consisting of hydrogen, methyl, cyano, nitro, polyfluoroalkyl of 1-3 carbon atoms, chloro, bromo, fluoro and alkylthio, with the proviso that from 2 to 5 of these are hydrogen, of which at least one of $A_1$, $A_2$, $A_3$, and $A_4$ and at least one of $B_1$, $B_2$, $B_3$ and $B_4$ are hydrogen; in a vehicle suitable for topical administration.

2. A composition according to claim 1 wherein $A_2$ and $B_2$ are other than hydrogen.

3. A composition according to claim 2 wherein $A_1$, $A_4$, $B_1$ and $B_4$ are hydrogen and $A_2$, $A_3$, $B_2$ and $B_3$ are independently trifluoromethyl, chloro, nitro, bromo, fluoro or methylthio.

4. A composition according to claim 2 wherein W is a bridge group of the formula

wherein R is alkyl of 1–7 carbon atoms, cyclopentenyl or benzyl.

5. A composition according to claim 4 wherein $A_1$, $A_2$, $A_3$, $A_4$, $B_1$, $B_2$, $B_3$ and $B_4$ are selected from the group consisting of hydrogen, nitro, trifluoromethyl, fluoro and chloro.

6. A composition according to claim 5 wherein $A_1$ and $B_1$ are hydrogen and $A_2$, $A_3$, $A_4$, $B_2$, $B_3$ and $B_4$ are all chloro.

7. A composition according to claim 5 wherein $A_1$, $A_3$, $B_1$ and $B_3$ are all hydrogen and $A_2$, $A_4$, $B_2$ and $B_4$ are all trifluoromethyl.

8. A composition according to claim 5 wherein the compound of formula I is N,N'-bis-[3,4-bis-(trifluoromethyl)phenyl]methylmalonamide.

9. A composition according to claim 5 wherein the compound of formula I is N,N'-bis-[3,4-bis-(trifluoromethyl)phenyl]methylmonothiomalonamide.

10. A composition according to claim 5 wherein the compound of formula I is N-[3,4-bis-(trifluoromethyl)-phenyl]-N-(5-chloro-2-nitrophenyl)methylmalonamide.

11. A composition according to claim 5 wherein the compound of formula I is N,N'-bis-(3-trifluoromethyl-4-nitrophenyl)benzylmalonamide.

12. A composition according to claim 5 wherein the compound of formula I is N-(3-trifluoromethyl-4-nitrophenyl)-N'-[3,5-bis-(trifluoromethyl)phenyl]methylmalonamide.

13. A composition according to claim 5 wherein the compound of formula I is N-(3-trifluoromethyl-4-nitrophenyl)-N'-(3-fluoro-4-nitrophenyl)methylmalonamide.

14. A composition according to claim 5 wherein the compound of formula I is N,N'-bis-(3-trifluoromethyl-4-nitrophenyl)isobutylmalonamide.

15. A composition according to claim 5 wherein the compound of formula I is N,N'-bis-[3,4-bis-(trifluoromethyl)phenyl](2-cyclopenten-1-yl)malonamide.

16. A composition according to claim 6 wherein the compound of formula I is N,N'-bis-(3,4,5-trichlorophenyl)methylmalonamide.

17. A composition according to claim 7 wherein the compound of formula I is N,N'-bis-[3,5-bis-(trifluoromethyl)phenyl]methylmalonamide.

18. A composition according to claim 1 wherein the amount of the compound of formula I is 0.1 to 3 percent by weight.

19. A composition according to claim 1 which is an ointment.

20. A composition according to claim 1 which is a cream.

21. The method of treating a dermatological disorder selected from the group consisting of acne, gram-positive bacterial infections and fungal infections which comprises administering topically to the affected area, the topical composition of claim 1.

22. The method of claim 21 wherein the dermatological disorder is acne.

23. The method of claim 21 wherein the dermatological disorder is a fungal infection.

24. The method of claim 21 wherein the dermatological disorder is a gram-positive bacterial infection.

25. A method according to claim 22, 23 or 24 wherein the compound of formula I administered is N,N'-bis-[3,5-bis-(trifluoromethyl)phenyl]methylmalonamide.

26. A method according to claim 22, 23 or 24 wherein the compound of formula I administered is N,N'-bis-[3,4-bis-(trifluoromethyl)phenyl]methylmonothiomalonamide.

* * * * *